Figure 1:
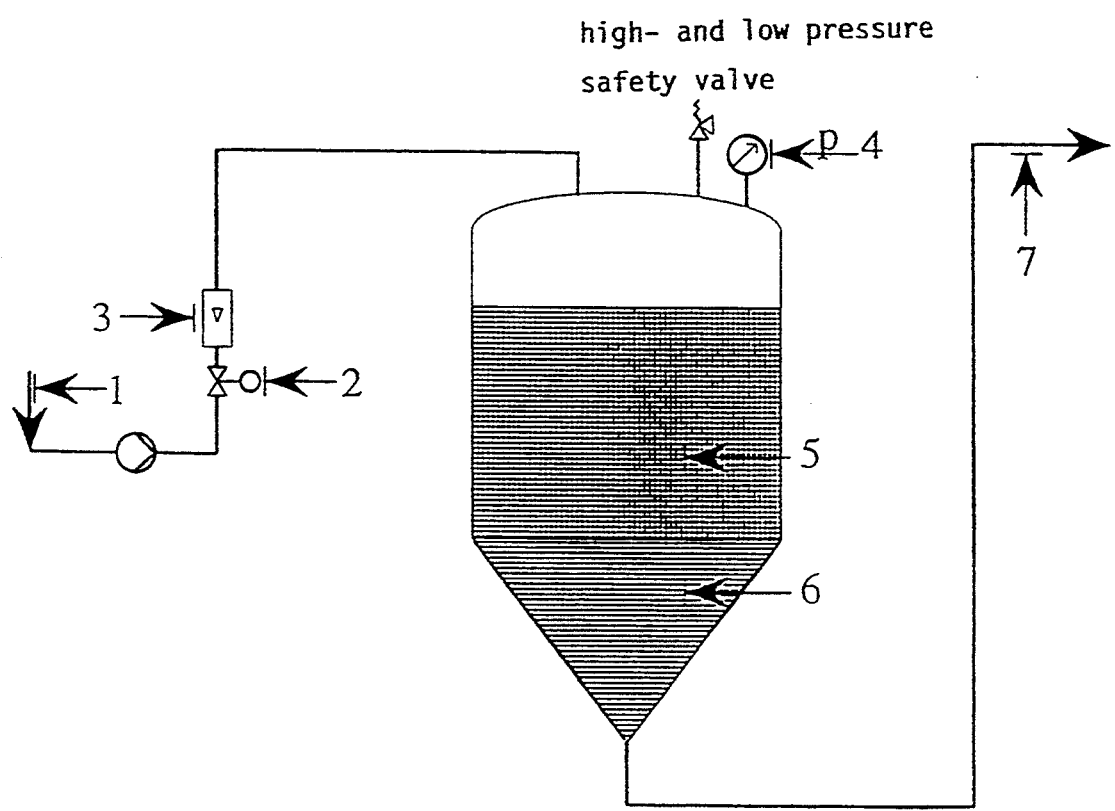

United States Patent [19]

Berg et al.

[11] Patent Number: 5,395,857
[45] Date of Patent: Mar. 7, 1995

[54] OPTIMIZED ION EXCHANGER BEDS FOR THE SYNTHESIS OF BISPHENOL A

[75] Inventors: Klaus Berg; Georg Malamet, both of Krefeld; Alfred Eitel, Dormagen; Claus Wulff, Krefeld, all of Germany

[73] Assignee: Bayer Aktiengesellschaft, Leverkusen, Germany

[21] Appl. No.: 220,612

[22] Filed: Mar. 31, 1994

[30] Foreign Application Priority Data

Apr. 13, 1993 [DE] Germany .................. 43 12 039.3

[51] Int. Cl.$^6$ ................. B01J 39/18; B01J 39/04; C07C 39/16; C07C 37/11
[52] U.S. Cl. ........................... 521/33; 521/25; 521/30; 521/32; 568/722; 568/723; 568/728
[58] Field of Search ............ 568/727, 728; 521/32, 521/33

[56] References Cited

U.S. PATENT DOCUMENTS

| | | | |
|---|---|---|---|
| 4,400,555 | 8/1983 | Mendiratta | 568/728 |
| 4,906,789 | 3/1990 | Grzywa | 568/727 |
| 5,146,007 | 9/1992 | Cipullo | 528/727 |
| 5,198,591 | 3/1993 | Kiedik | 568/727 |
| 5,302,774 | 4/1994 | Berg | 528/727 |

OTHER PUBLICATIONS

F. Helfferica, "Ion Exchange" (1962) 546–547 McGraw-Hill (New York).
Derwent Database, JP 4001149, (Jan. 6, 1992).
Chemical Abstracts, 118:1 (Apr. 1932).
Chemical Abstracts 116:818 (Feb. 1992).
Chemical Abstracts, 120:138 (1994).

*Primary Examiner*—Fred Zitomer
*Attorney, Agent, or Firm*—Connolly & Hutz

[57] ABSTRACT

The invention relates to a process for increasing (improving) the volume/time yield of fixed-bed reactors in the production of bisphenol A.

2 Claims, 1 Drawing Sheet

OPTIMIZED ION EXCHANGER BEDS FOR THE SYNTHESIS OF BISPHENOL A

This invention relates to a process for increasing (improving) the volume/time yield of fixed-bed reactors in the production of bisphenol A.

Processes for the synthesis of bisphenol A by ion exchanger catalysis are known (see, for example, U.S. Pat. Nos. 4,391,997, 4,400,555, 4,590,303, JP-A 8 272 972, PL-A 96 436, CS-A 183 069, EP-A 210 366, etc.).

It is known that, in the industrial production of bisphenol A (BPA), a mixture of excess phenol and acetone is passed through a cylindrical fixed-bed reactor filled with sulfonic acid ion exchanger resins (based on polystyrene) and is then worked up. The direction of flow of the mixture may be either downwards or upwards as required. Each of these feed directions has advantages and disadvantages. Where the feed direction is downwards, the pressure loss through the ion exchanger bed is a major problem on account of the resulting impairment of throughput. The pressure loss can be caused, for example, by the compressibility of the ion exchanger resin used. The spherical resin particles can be deformed under pressure into a lenticular shape, thus leading to an exponential reduction in throughput. Firm compression of the catalyst bed can promote the formation of flow channels so that flow through the reactor is not uniform. Accordingly, the quantity of catalyst used as a whole may not be fully utilized.

A process has now been found in which the pressure loss in the industrial production of bisphenol A from acetone and phenol in a cylindrical fixed-bed reactor filled with sulfonic acid ion exchanger resins in large quantities can be greatly limited. The capacity of the fixed-bed reactor can thus be considerably increased. The capacity is no longer limited by the amount of feed and the corresponding pressure losses. It is determined by the acetone conversion.

Hydraulic problems of the type in question have been observed in particular with sulfonic acid ion exchangers having a low degree of crosslinking ($\leq 2\%$). On the other hand, these very ion exchangers represent an optimum in regard to reactivity and selectivity in the synthesis of bisphenol A.

Although, with ion exchanger resins having a higher degree of crosslinking ($\geq 2.5\%$), the hydraulic problems of the corresponding beds decrease with increasing degree of crosslinking, the reactivity and selectivity of such resins in the synthesis of BPA also decrease to a considerable extent.

One way of improving the hydraulic quality of lightly crosslinked resin beds is to cover some of the sulfonic acid groups with cations. Partial covering with $+NH_3-CH_2-CH_2-SH$ or similar systems, as described for example in DE-A 3 619 450 and U.S. Pat. No. 3,394,089, is particularly advantageous. In addition to embrittlement and hence greater rigidity of the ion exchanger, a catalytic effect of the groups in the synthesis of BPA is also observed.

However, the useful life of such systems is shortened by a factor of approximately 10 compared with unmodified resin systems by deactivation of the cocatalytic unit and is therefore uneconomical. The necessary subsequent regeneration of the large quantities of Lewatit is time-consuming and expensive and has to be replaced by an equally large quantity of fresh ion exchanger to maintain the output of BPA.

A resin bed model optimally combining the advantages of the respective resins has now been found. The lower layer of the ion exchanger bed in the reactor (volume-wise 75–85%) consists of an unmodified sulfonic acid ion exchanger having a low degree of crosslinking ($\leq 2\%$). The upper layer (volume-wise 15–25%) may consist of a) an ion exchanger having a higher degree of crosslinking ($\geq 2\%$) or b) a resin having a low degree of crosslinking ($\leq 2\%$), in which 1 to 25 mol-% of the sulfonic acid groups have been covered with species containing alkyl-SH (for example mercaptoethyl amines as described in DE-A 3 619 450 or in U.S. Pat. No. 334,940,089) (ionic fixing).

Accordingly, the present invention relates to ion exchanger beds for increasing the volume/time yield of fixed-bed reactors in the production of bisphenol A from phenol and acetone in cylindrical fixed-bed reactors filled with gel-form or macroporous sulfonic acid ion exchanger resins, characterized in that a) the lower layer of the bed consists of a resin having a low degree of crosslinking ($\leq 2\%$) and makes up 75 to 85% by volume of the bed as a whole and b) the upper layer of the bed, which makes up 15 to 25% by volume, consists either of a resin having a higher degree of crosslinking ($\geq 2\% \leq 4\%$), in which 1 to 25 mol-% of the sulfonic acid groups may be covered with species containing alkyl-SH units (ionic fixing) or c) of a resin having a low degree of crosslinking ($\leq 2\%$), in which 1 to 25 mol-% of the sulfonic acid groups are covered with species containing alkyl-SH units (ionic fixing).

From the hydraulic point of view, resin beds according to the invention behave as if the upper rigid resin layer were the sole filling of the reactor, i.e. the capacity of the reactor is no longer determined by the hydraulics of the filling, but instead by the acetone conversion.

In addition to its favorable hydraulic properties in the synthesis of BPA, the layer type of a) and c) surprisingly shows the excellent reactivity and selectivity behavior of a resin bed consisting solely of a lightly crosslinked ion exchanger type ($\leq 2\%$) to the sulfonic acid groups of which alkyl-SH species have been partly ionically fixed. In the event of deactivation of the uppermost ion exchanger layer where it consists of the a) +c) type, it may be regenerated or disposed of in an economically reasonable manner by virtue of its small volume.

In the case of the layer type of a) and b) which, although having excellent hydraulic properties, does not show the excellent selectivity and reactivity behavior of the layer type of a) and c), performance can be improved to an almost equivalent level by partial covering of the sulfonic acid units (1–25 mol-%) of the more highly crosslinked, upper resin layer with alkyl-SH units (for example mercaptoethylamine, thiazolidine).

The modified and unmodified ion exchanger resins are prepared in known manner (as described, for example, in U.S. Pat. No. 3,394,089 or in DE-A 3 619 450). The bisphenol A is produced and worked up continuously using known methods and equipment.

The ion exchanger beds according to the invention for the synthesis of bisphenol A represent an optimum in regard to hydraulics, selectivity and reactivity for the synthesis of BPA.

EXAMPLES

FIG. 1 illustrates the type, construction and mode of operation of the reactor.

A mixture of phenol, recycled mother liquor (consisting of phenol, bisphenol A and secondary products) and acetone is introduced into the reactor from above through a pipe (1). The reactor is normally filled with ion exchanger (5) to between 50 and 80% of its total volume. In the lower conical part (6) of the reactor, there is a layer of mineral material as carrier for the resin bed. The reaction mixture flows downwards through the fixed bed. The reaction solution issues from the reactor at its lower end and is then worked up.

The feed volume is normally controlled by a pneumatic control valve (2) and a throughflow meter (3). The feed temperature is in the range from 55° to 62° C.; the discharge temperature is in the range from 75° to 85° C. The reactor is operated under adiabatic conditions. Heat losses are avoided by insulation and backup heating. The pressure loss through the Lewatit bed is measured in the upper part of the reactor (4). For safety reasons, introduction of the reaction mixture is stopped when the pressure loss caused by the Lewatit bed reaches 2 bar.

The composition by weight of the reaction mixture introduced into the reactor may vary within the following limits: phenol 75-85% by weight, bisphenol A and secondary products 12-20% by weight, acetone 2-6% by weight.

Example 1 (Comparison)

A reactor of the type shown in FIG. 1 with a cross-sectional area of 25 m$^2$ and a height of the cylindrical unit of 5 m is filled with 100 m$^3$ phenol-moist unmodified resin with a degree of crosslinking of 2%. The reactor is charged with 17 m$^3$/h reaction mixture (feed temperature 60° C.). The following performance data were determined:

| | |
|---|---|
| Pressure loss in the reactor: | 1.7 bar |
| Acetone conversion in the reactor: | 96.5% |
| Selectivity of the reaction: | 96% |

The feed rate cannot be increased with this reactor bed because a few hundred liters more result in an exponential increase in pressure and hence in activation of the safety cutout.

Example 2

(Layer type a)

A reactor according to Example 1 is filled with 80 m$^3$ phenol-moist unmodified ion exchanger with a degree of crosslinking of 2% and then with 20 m$^3$ of a phenol-moist, unmodified resin with a degree of crosslinking of 4%.

The following performance data of the resin bed in the synthesis of BPA were determined:

| | | |
|---|---|---|
| 1. | Feed rate reaction mixture | 17 m$^3$/h (60° C.) |
| | Reactor pressure loss: | 0.1 bar |
| | Acetone conversion: | 96.0% |
| | Selectivity of the reaction: | 95.1% |
| 2. | Feed rate reaction mixture | 20 m$^3$/h (60° C.) |
| | Reactor pressure loss: | 0.15 bar |
| | Acetone conversion: | 93.0% |
| | Selectivity of the reaction: | 94.5% |

Example 3

(Layer type a) modified)

A reactor according to Example 1 is filled with 80 m$^3$ phenol-moist unmodified ion exchanger with a degree of crosslinking of 2% and then with 20 m$^3$ of a phenol-moist resin with a degree of crosslinking of 4% in which 3 mol-% of the sulfonic acid groups have been covered with mercaptoethylamine. The following performance data of the resin bed in the synthesis of BPA were determined:

| | |
|---|---|
| Feed rate reaction mixture | 20 m$^3$/h (60° C.) |
| Reactor pressure loss: | 0.15 bar |
| Acetone conversion: | 96.9% |
| Selectivity of the reaction: | 97.9% |

Example 4

(Layer type b)

A reactor according to Example 1 is filled with 80 m$^3$ phenol-moist unmodified ion exchanger with a degree of crosslinking of 2% and then with 20 m$^3$ of a phenol-moist 2% crosslinked resin in which 15 mol-% of the sulfonic acid groups have been covered with mercaptoethyl amine. The following performance data of the resin bed were determined:

| | | |
|---|---|---|
| 1. | Feed rate reaction mixture | 17 m$^3$/h (60° C.) |
| | Reactor pressure loss: | 0.25 bar |
| | Acetone conversion: | 99.9% |
| | Selectivity of the reaction: | 98.5% |
| 2. | Feed rate reaction mixture | 23 m$^3$/h (60° C.) |
| | Reactor pressure loss: | 0.6 bar |
| | Acetone conversion: | 97.5% |
| | Selectivity of the reaction: | 98.0% |

We claim:

1. In an ion exchange bed for producing bisphenol A from phenol and acetone in a fixed bed reactor containing gel-form or macroporous sulfonic acid ion exchanger resins, the improvement comprising providing the resin as a two-layer bed wherein:

the lower layer of the bed comprises an unmodified resin having a low degree of crosslinking, less than or equal to 2%, and comprises 75 to 85% of the bed volume as a whole; and the upper layer of the bed, which comprises 15 to 25% of the bed volume as a whole, comprises either a resin having a higher degree of crosslinking than the lower bed, from equal to or greater than 2% to less than or equal to 4%, in which 1 to 25 mol % of the sulfonic acid groups are optionally covered with species containing alkyl-SH groups by ionic fixing, or a resin having a low degree of crosslinking, less than or equal to 2%, in which 1 to 25 mol % of the sulfonic acid groups are covered with species containing alkyl-SH groups by ionic fixing.

2. In a process for preparing bisphenol A from phenol and acetone in a fixed bed reactor containing gel-form or macroporous sulfonic acid ion exchanger resins in the form of a resin bed, the improvement which comprises utilizing as the resin bed the two layer bed as claimed in claim 1.

* * * * *